United States Patent [19]

Brands

[11] Patent Number: 5,648,501
[45] Date of Patent: Jul. 15, 1997

[54] PROCESS FOR SYNTHESIZING CARBAPENEM SIDE CHAIN INTERMEDIATES

[75] Inventor: Karel M. J. Brands, Hoboken, N.J.

[73] Assignee: Merck & Co., Inc., Rahway, N.J.

[21] Appl. No.: 681,025

[22] Filed: Jul. 22, 1996

Related U.S. Application Data

[60] Provisional application No. 600/001891, Aug. 4, 1995.
[51] Int. Cl.[6] .................................................. C07D 495/08
[52] U.S. Cl. .................................................... 548/453
[58] Field of Search .................................... 548/453

[56] References Cited

U.S. PATENT DOCUMENTS 5,322,952  6/1994  Sunagawa et al. ................... 548/453

OTHER PUBLICATIONS

Heterocycles, vol. 41, pp. 147–159 (1995), by Matsumura, et al.
CA 119: 271142w Preparation of . . . intermediates. Sunagawa et al. p. 996 1993.
CA 122: 239477k An efficient . . . derivatives. Matsumura et al. p. 1038 1995.

*Primary Examiner*—Joseph McKane
*Attorney, Agent, or Firm*—Richard C. Billups; Mark R. Daniel

[57] ABSTRACT

A process of synthesizing a compound of the formula I:

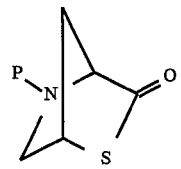

is described. A compound of the formula II:

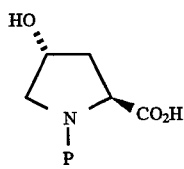

is reacted with diphenylphosphinic chloride to activate the carboxylic acid group, and then reacted with methanesulfonyl chloride to produce a compound of formula IV:

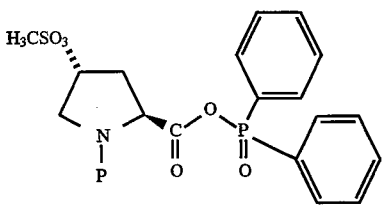

Compound IV is then reacted with $Na_2S$ in water to produce a compound of formula I.

9 Claims, No Drawings

PROCESS FOR SYNTHESIZING CARBAPENEM SIDE CHAIN INTERMEDIATES

CROSS REFERENCE TO RELATED APPLICATIONS

This application is a non-provisional application based upon U.S. application Ser. No. 60/001,891, filed provisionally in the U.S. on Aug. 4, 1995, priority of which is claimed hereunder.

BACKGROUND OF THE INVENTION

The present invention relates to the synthesis of carbapenem side chains, and in particular, to side chains or portions thereof containing a pyrrolidine group, which is bonded to the carbapenem nucleus through a thioether linkage. Typically, the pyrrolidine is a portion of the side chain, and is substituted at the two position with any of a variety of substituents.

Conventionally, these intermediate compounds are prepared from a 4-hydroxyproline derivative of the formula:

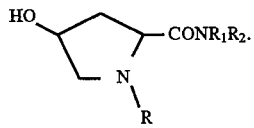

Such synthetic schemes typically require the extensive use of protecting groups.

Similarly, a method of converting trans-4-hydroxy-L-proline to a thiolactone of the formula:

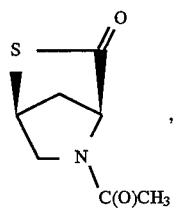

has been described. However, this thiolactone is unsuitably protected for large scale synthesis of carbapenem antibiotics.

EP 551 993 A1 published on Jul. 21, 1993 relates to a synthesis which utilizes active esterifying agents and base, followed by treatment with hydrogen sulfide and base.

The present invention is an improvement over these other processes, utilizing an activating agent, namely, diphenylphosphinic chloride, which surprisingly improves the results which are achieved when commercial quantities are synthesized.

SUMMARY OF THE INVENTION

A process for synthesizing a compound of the formula I:

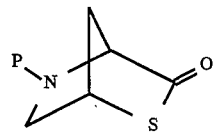

is described wherein P is a protecting group selected from t-butoxycarbonyl, p-nitrobenzyloxycarbonyl, benzyloxycarbonyl and allyloxycarbonyl, comprising (a) reacting a compound of formula II:

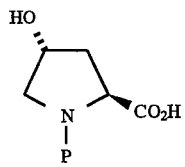

wherein P is as previously defined with diphenylphosphinic chloride to produce a compound of formula III:

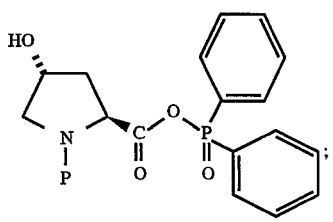

(b) reacting compound III with methanesulfonyl chloride to produce a compound of formula IV:

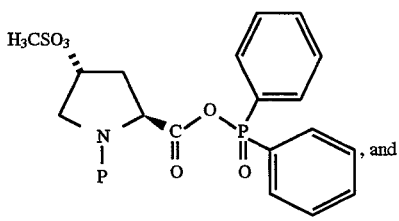

(c) combining compound IV with $Na_2S$ in water to produce a compound of formula I.

Another aspect of the process described herein relates to a process for producing a compound of the formula V:

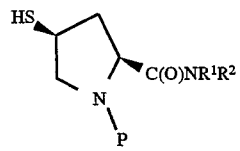

wherein P is a protecting group selected from t-butoxycarbonyl, p-nitrobenzyloxycarbonyl, benzyloxycarbonyl and allyloxycarbonyl;

$R^1$ and $R^2$ are independently selected from hydrogen, aryl and heteroaryl, said aryl and heteroaryl groups being unsubstituted or substituted with from 1–3 groups selected from the group consisting of: $C_{1-4}$ alkyl, $C_{1-4}$ alkoxy, $C_{1-4}$ alkylthio, halo, hydroxy, $CO_2H$, $CO_2C_{1-4}$ alkyl, $NH_2$, $NHC_{1-4}$ alkyl, $N(C_{1-4}$ alkyl$)_2$, $SO_3H$, CN, $SO_2NH_2$, $SO_2C_{1-4}$ alkyl, aryl and heteroaryl;

comprising:

(a) reacting a compound of the formula II:

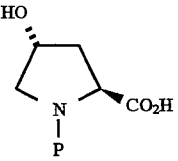

wherein P is as previously defined with diphenylphosphinic chloride to produce a compound of the formula III:

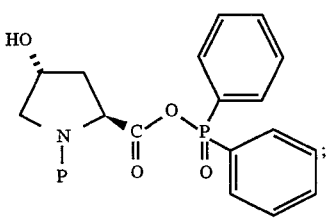

(b) reacting compound III with methanesulfonyl chloride to produce a compound of formula IV:

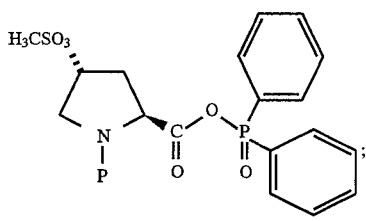

(c) combining compound IV with Na$_2$S in water to produce a compound of formula I:

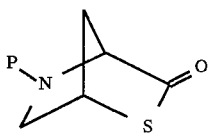

and (d) reacting compound I with NHR$^1$R$^2$ wherein R$_1$ and R$^2$ are as previously defined to produce a compound of formula V.

DETAILED DESCRIPTION OF THE INVENTION

The following definitions apply to the terms used herein unless otherwise defined.

Alkyl and the alkyl portions of substituent groups include monovalent hydrocarbon chains containing from 1–4 carbon atoms which are straight or branched as appropriate.

Aryl refers to 6–10 membered mono- and bicyclic ting systems, containing carbon atoms with alternating (resonating) double bonds. Preferred aryl groups are phenyl and naphthyl.

Heteroaryl refers to aromatic 5–10 membered mono- and bicyclic ting systems, containing from 1–4 heteroatoms, O, S or N. Preferred nitrogen containing monocyclic heteroaryl groups include pyridyl, pyrimidinyl, pyrazinyl, pyrrolyl, imidazolyl, thiazolyl, oxazolyl and 1, 2, 4-triazolyl. Preferred heteroaryl groups containing oxygen as the only heterotom include furanyl. Preferred heteroaryl groups containing sulfur as the only heterotom include thienyl.

Preferred bicyclic heteroaryl groups include benzthiazolyl, benzimidazolyl, quinolinyl and isoquinolinyl, indolyl and isoindolyl.

When substituted, the aryl and heteroaryl groups may be substituted with 1–3 groups selected from the group consisting of: $C_{1-4}$ alkyl, $C_{1-4}$ alkoxy, $C_{1-4}$ alkylthio, halo, hydroxy, $CO_2H$, $CO_2C_{1-4}$ alkyl, $NH_2$, $NHC_{1-4}$ alkyl, $N(C_{1-4}$ alkyl$)_2$, $NHC(O)C_{1-4}$ alkyl, $SO_3H$, CN, $SO_2NH_2$, $SO_2C_{1-4}$ alkyl, aryl and heteroaryl.

When necessary, the substituents which are optionally present on aryl and heteroaryl can be in protected form. Examples of suitable protecting groups are: t-butylmethoxyphenylsilyl, t-butoxydiphenylsilyl, trimethylsilyl, triethylsilyl, o-nitrobenzyloxycarbonyl, p-nitrobenzyloxycarbonyl, benzyloxycarbonyl, t-butyloxycarbonyl, 2,2,2-trichloroethyloxycarbonyl benzhydryl, o-nitrobenzyl, p-nitrobenzyl, 2-naphthylmethyl, allyl, 2-chloroallyl, benzyl, 2,2,2-trichloroethyl, trimethylsilyl, t-butyldimethylsilyl, t-butyldiphenylsilyl, 2-(trimethylsilyl) ethyl, phenacyl, p-methoxybenzyl, acetonyl, p-methoxyphenyl, 4-pyridyl-methyl, t-butyl and allyloxycarbonyl. Preferred hydroxyl protecting groups are trimethylsilyl and triethylsilyl. Preferred carboxyl protecting groups are p-nitrobenzyl and allyl.

Many other suitable hydroxyl and carboxyl protecting groups are known in the art. See, e.g., Greene, T. W., et al. *Protective Groups in Organic Synthesis*, John Wiley & Sons, Inc., 1991.

P represents a protecting group on the proline nitrogen atom. Values of P are selected from t-butoxycarbonyl (t-BOC), p-nitrobenzyloxycarbonyl, benzyloxycarbonyl and allyloxycarbonyl. The most preferred P groups are t-butoxycarbonyl and p-nitrobenzyloxycarbonyl (PNZ).

Compound II used herein as a starting material is N protected trans-4-hydroxy-L-proline. The 2-carboxyl group is activated using the compound diphenylphosphinic chloride, which is reacted with compound II in a solvent in the presence of excess base. Solvents which are useful herein include dichloromethane, acetonitrile, toluene and tetrahydrofuran, or mixtures thereof. Bases which are useful for this reaction include trialkylamines. Preferred trialkylamines include diisopropylethylamine (DIPEA) and triethylamine.

Typically an amount of diphenylphosphinic chloride which is about equimolar to the starting compound can be used. The reaction between compound II and diphenylphosphinic chloride is typically nm at reduced temperature, below about 0° C. to as low as about –40° C. Preferably, the reaction temperature is maintained at about –10° C.

Compound III, with the diphenylphosphinyloxycarbonyl group at position two, is reacted with methanesulfonyl chloride (MsCl) in the same pot to produce compound W. This reaction is conducted in a solvent, in the presence of a slight molar excess of pyridine, collidine, lutidine and the like, using a slight molar excess of MsCl. This mesylation reaction may be conducted over about 1–4 hours, at a reduced temperature, e.g., about 0° C. to as low as about –40° C. Preferably, the reaction temperature is maintained at about –10° C.

Compound IV is thereafter combined with sodium sulfide and water to form the thiolactone I. Essentially the reaction can be conducted at about –10° C. to about room temperature. Preferably the sodium sulfide and water are added quickly, and the reaction is aged for several hours at ambient temperature.

After conversion of compound IV to compound I is complete, the latter is combined in the same pot with ammonia or a primary or secondary amine to form compounds of formula V. At this point, other solvents, such as isopropanol, ethanol, n-propanol, toluene, acetonitrile, ethyl acetate and others are added to improve crystallization of compound V, and thus facilitate its isolation. Also, addition of a trialkyl or triaryl phosphine, e.g., tri-n-butylphosphine, at this stage may be useful in reducing the formation of disulfides corresponding to compound V.

Most primary and secondary amines HNR$^1$R$^2$ wherein R$^1$ and/or R$^2$ represent H, aryl or heteroaryl react with compound I upon slight heating. Generally, the reaction proceeds from about RT to about 100° C. over a few minutes to several hours.

The invention described herein can be conducted in essentially a single reaction vessel, thus allowing for economical production of compounds V from compound II.

The invention is further illustrated with the following non-limiting examples.

EXAMPLE ONE

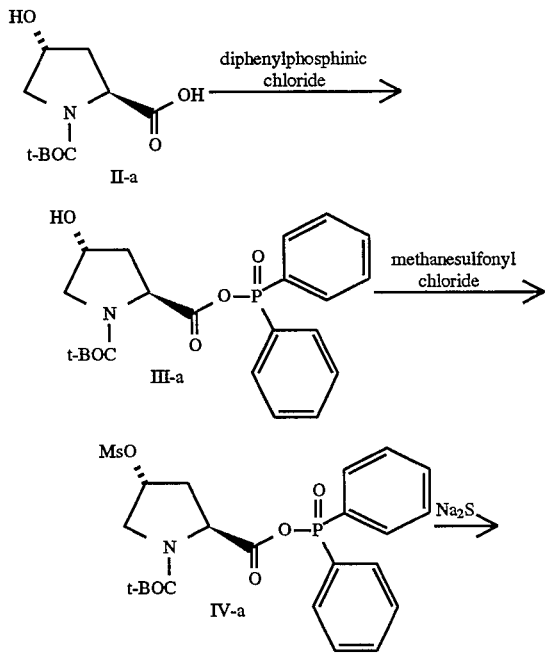

A. Synthesis of trans -N-t-butoxycarbonyl-2-diphenylphosphinyloxycarbonyl-4-hydroxy-L-proline

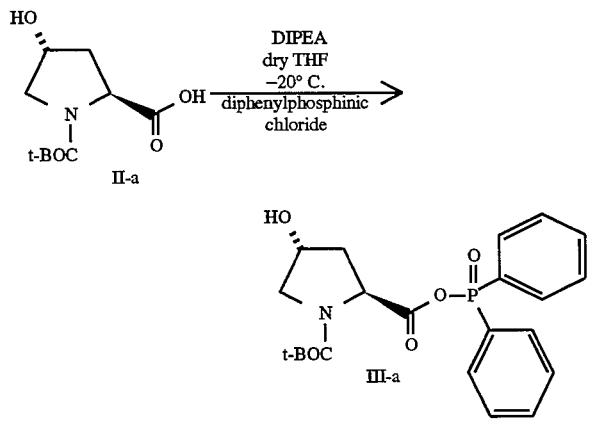

A solution of compound II-a (35.0 g, 151 mmol.) and DIPEA (60 mL, 344 mmol) in dry THF (1.0 L) was combined over 20 min with a solution of diphenylphosphinic chloride (37.5 g, 155 mmol) in THF (50 mL) at −20° C. The reaction mixture was stirred at −20° C. for 90 minutes to produce compound III-a, which can be isolated and characterized or used in the next part without isolation.

B. Synthesis of trans-N-t-butoxycarbonyl-2-diphenylphosphinyloxycarbonyl-4-methanesulfonyloxy-L-proline

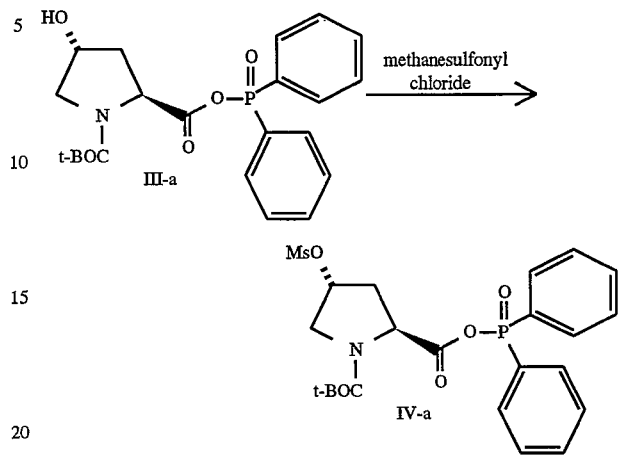

Without isolation and characterization, after stirring the reaction mixture from part A for 90 minutes at −20° C., pyridine (13.0 mL, 161 mmol) was added followed by a solution of methanesulfonyl chloride (19.8 g, 171 mmol) in THF (50 mL) over 15 minutes. The reaction mixture was stirred at −20° C. for 2 hours and allowed to warm to −5° C. over an additional 30 minutes producing compound IV-a. The methanesulfonyl substituted compound can be isolated and characterized, or used in the next reaction without isolation and characterization.

C. Synthesis of N-t-butoxycarbonyl-2-thia-5-azabicyclo [2.2.1]heptan-3-one

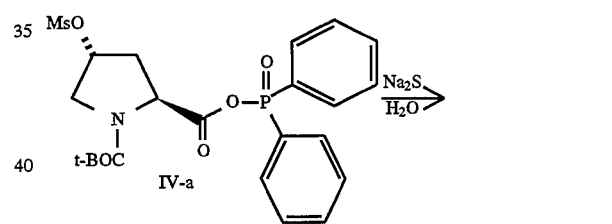

After allowing the reaction from part B to warm to −5° C., a solution of $Na_2S \cdot H_2O$ (45.0 g, 187 mmol) in $H_2O$ (60 mL) was added in one portion producing a biphasic reaction mixture. The biphasic mixture was allowed to warm to room temperature and was stirred for 6 hrs. The resulting suspension was then partitioned between toluene and water.

The organic layer was washed with HCl (2.0M), $NaHCO_3$ (1.0M) and brine, dried over $MgSO_4$ and concentrated in vacuo to produce an oily residue. Crystallization of the oily residue from ether/ethyl acetate provided the title compound (29.4 g, 88 mmol).

mp 91° C.; $[\alpha]_D = -88.0°$ (c=1.01; $CHCl_3$).

$^1$H-NMR ($CD_2Cl_2$, −20° C.; 400 MHz) δ1.42 (s, $^3$H), 2.07 (dt, J 2.5, J 11.3, 1H), 2.13 (m, J 11.3, 1H), 3.48 and 3.53 (m, J 1.1, J 10.2, 1H), 3.74, (m, J 2.8, J 10.1, 1H), 4.11 (m, 1H), 4.42 and 4.53 (m, J 0.9, 1H); $^{13}$C-NMR ($CD_2Cl_2$, −20° C.; 100 MHz) δ29.9/30.0(q), 43.3/43.9(1), 49.9/50.6 (d), 54.3/54.7 (t), 65.3/66.1 (d), 82.5/82.6 (s), 155.5/155.7 (s), 201.1/201.6 (s).

EXAMPLE TWO

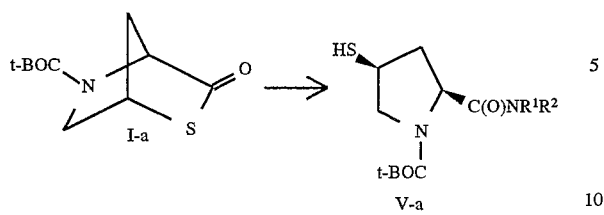

Thiolactone I-a from Example One without isolation, can be combined with the amine shown below in column one to produce the cis N-protected 4-thiol substituted proline derivative shown below in column two.

TABLE ONE

| Amine | Product V-a |
|---|---|
| (1) NH₄Cl | HS—[pyrrolidine]—C(O)NH₂, N-t-BOC |
| (2) aniline (C₆H₅NH₂) | HS—[pyrrolidine]—C(O)NH—C₆H₅, N-t-BOC |
| (3) 3-aminobenzoic acid | HS—[pyrrolidine]—C(O)NH—C₆H₄—CO₂H, N-t-BOC |
| (4) 5-amino-2-carboxythiophene (H₂N—thiophene—CO₂H) | HS—[pyrrolidine]—C(O)NH—thiophene—CO₂H, N-t-BOC |

(1) 4.0 eq. of $NH_4Cl$ in $Et_3N$; solvent $CH_3OH$; reaction time: 30 min at RT;
(2) 1.25 eq. of aniline; solvent toluene; reaction time: 2 hrs at 100° C.;
(3) 1.25 eq. of 3-aminobenzoic acid; solvent toluene; reaction time: 2 hrs at 100° C.;
(4) 1.25 eq. of 5-amino-2-carboxythiophene; solvent toluene; 2 hrs at 100° C.;

EXAMPLE THREE

Using the procedures set forth in Example One, Part A, the compounds of column one are reacted with diphenylphosphinic chloride to produce the compounds in column two.

TABLE TWO

| (II-b) | (III-b) |
|---|---|
| HO—[pyrrolidine]—CO₂H, N-C(O)O-CH₂-C₆H₄-NO₂ | HO—[pyrrolidine]—CO₂P(O)(Ph)₂, N-C(O)O-CH₂-C₆H₄-NO₂ |

Ph = phenyl

TABLE TWO-continued

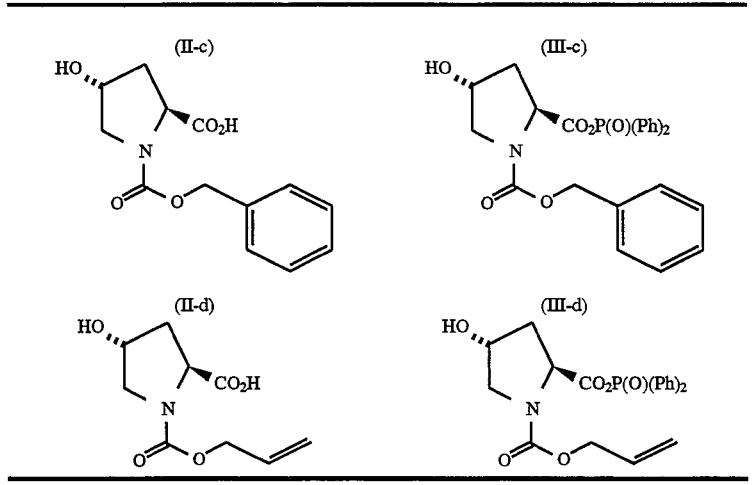

EXAMPLE FOUR

Using the procedures set forth in Example One, Part B, the compounds of column one are reacted with methanesulfonyl chloride to produce the compounds in column two.

TABLE THREE

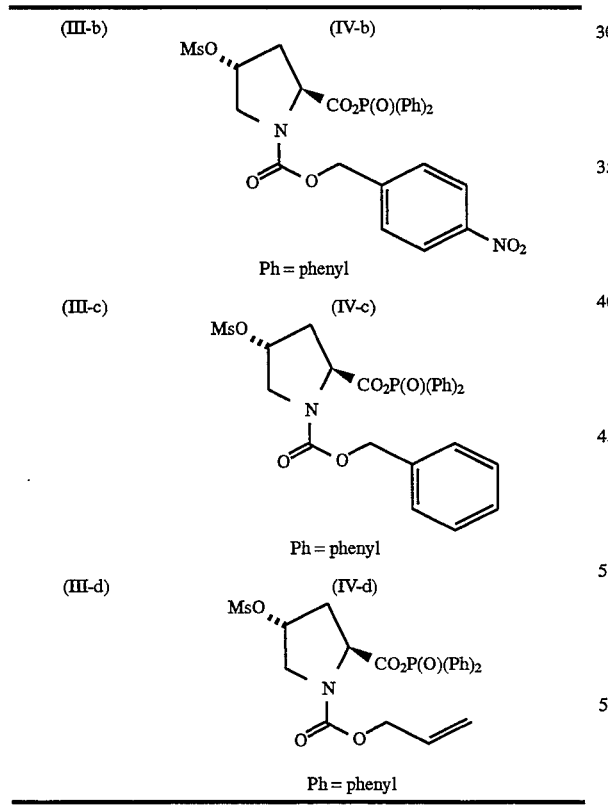

EXAMPLE FIVE

Using the procedures set forth in Example One, Part C, the compounds of column one are reacted with $Na_2S$ in water to produce the compounds in column two.

TABLE FOUR

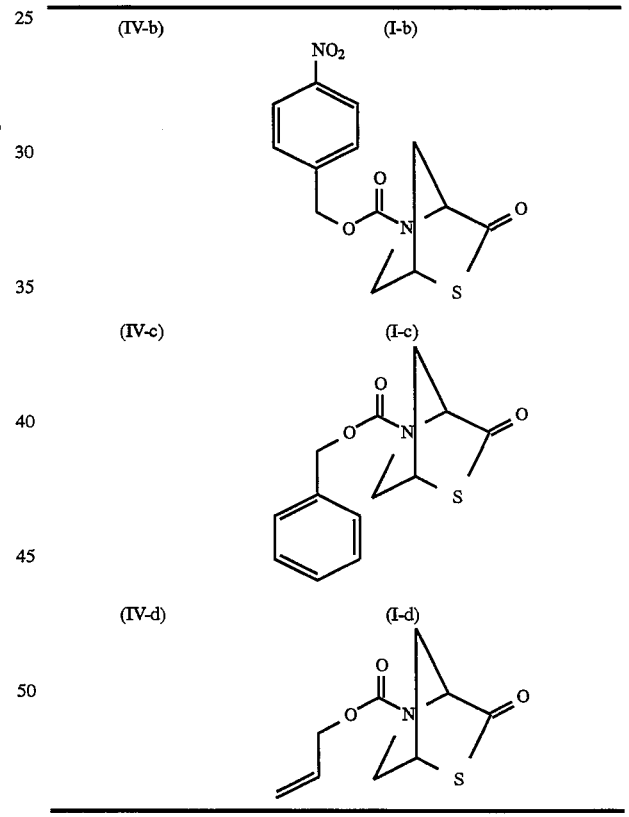

EXAMPLE SIX

Using the procedures set forth in Example Two, the compounds of column one are reacted with the amine in column two to produce the compounds in column three.

TABLE FIVE
| | Amine NHR¹R² | Pyrrolidine |
|---|---|---|
| (I-b) | (1) NH₄Cl | (V-b-1)[1] 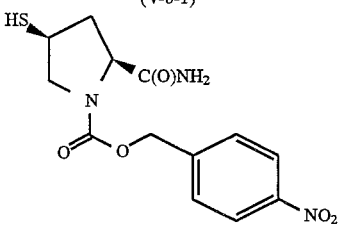 |
| (I-b) | (2) 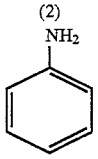 | (V-b-2)[1] 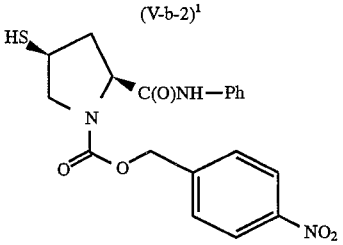 Ph = Phenyl |
| (I-b) | (3) 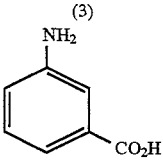 | (V-b-3)[1] 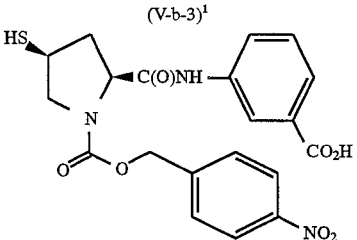 |
| (I-b) | (4) 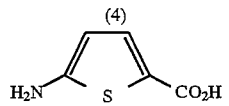 | (V-b-4)[1] 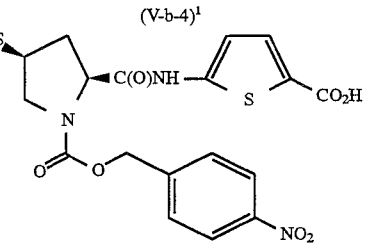 |
| (I-c) | (1) NH₄Cl | (V-c-1)[1] 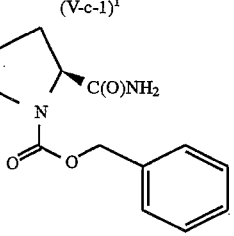 Ph = Phenyl |
| (I-c) | (2) 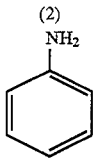 | (V-c-2)[1] 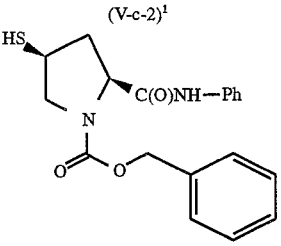 Ph = Phenyl |

TABLE FIVE-continued

| Amine NHR¹R² | | Pyrrolidine | |
|---|---|---|---|
| (I-c) | (3) 3-aminobenzoic acid | (V-c-3)[1] | pyrrolidine structure with HS, Cbz, C(O)NH-3-carboxyphenyl |
| (I-c) | (4) 5-amino-2-thiophenecarboxylic acid | (V-c-4)[1] | pyrrolidine structure with HS, Cbz, C(O)NH-thiophene-CO₂H |
| (I-d) | (1) NH₄Cl | (V-d-1)[1] | pyrrolidine structure with HS, Alloc, C(O)NH₂ |
| (I-d) | (2) aniline | (V-d-2)[1] | pyrrolidine structure with HS, Alloc, C(O)NH—Ph |
| | | Ph = Phenyl | |
| (I-d) | (3) 3-aminobenzoic acid | (V-d-3)[1] | pyrrolidine structure with HS, Alloc, C(O)NH-3-carboxyphenyl |
| (I-d) | (4) 5-amino-2-thiophenecarboxylic acid | (V-d-4)[1] | pyrrolidine structure with HS, Alloc, C(O)NH-thiophene-CO₂H |

[1]Tri-n-butylphosphine may be added.

While certain preferred embodiments have been described herein in detail, numerous alternative embodiments are contemplated as falling within the scope of the invention.

What is claimed is:

1. A process for synthesizing a compound of the formula I:

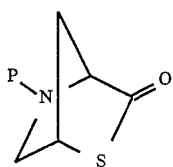

wherein P is a protecting group selected from t-butoxycarbonyl, p-nitrobenzyloxycarbonyl, benzyloxycarbonyl and allyloxycarbonyl;

comprising (a) reacting a compound of the formula II:

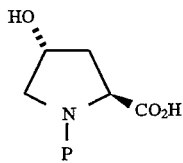

wherein P is as previously defined with diphenylphosphinic chloride to produce a compound of the formula III:

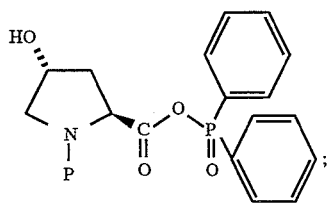

(b) reacting compound III with methanesulfonyl chloride to produce a compound of formula IV:

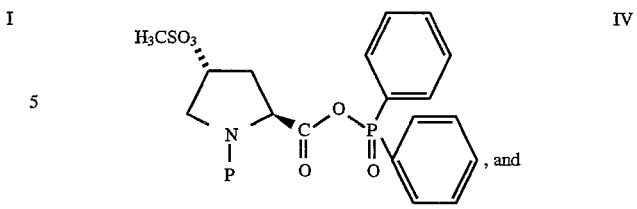

(c) combining compound IV with $Na_2S$ in water to produce a compound of formula I.

2. A process in accordance with claim 1 wherein compound II is reacted with diphenylphosphinic chloride in the presence of a base.

3. A process in accordance with claim 2 wherein the base is a trialkylamine.

4. A process in accordance with claim 3 wherein the trialkylamine is selected from the group consisting of diisopropylethylamine and triethylamine.

5. A process in accordance with claim 1 wherein compound III is reacted with methanesulfonyl chloride to produce a compound of formula IV in the presence of a base.

6. A process in accordance with claim 5 wherein the base is selected from the group consisting of pyridine, collidine and lutidine.

7. A process in accordance with claim 1 wherein $Na_2S$ in water is reacted with compound IV to produce a compound of formula I at a temperature of about −10° C. to about room temperature.

8. A process in accordance with claim 1 wherein P represents t-butoxycarbonyl or p-nitrobenzyloxycarbonyl.

9. A process in accordance with claim 1 wherein the $Na_2S$ in water is reacted with compound IV to produce a compound of formula I at a temperature of about −10° C. to about room temperature.

* * * * *